(12) United States Patent
Ogilvie et al.

(10) Patent No.: US 7,909,857 B2
(45) Date of Patent: Mar. 22, 2011

(54) DEVICES AND METHODS FOR CORRECTING SPINAL DEFORMITIES

(75) Inventors: James W. Ogilvie, Brighton, UT (US); Fred J. Molz, IV, Birmingham, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 406 days.

(21) Appl. No.: 12/055,624

(22) Filed: Mar. 26, 2008

(65) Prior Publication Data
US 2009/0248075 A1 Oct. 1, 2009

(51) Int. Cl.
*A61B 17/88* (2006.01)
(52) U.S. Cl. .................................................. 606/279
(58) Field of Classification Search ........... 606/246–279
See application file for complete search history.

(56) References Cited

U.S. PATENT DOCUMENTS

| 4,003,376 A | 1/1977 | McKay et al. |
| 4,848,328 A | 7/1989 | Laboureau et al. |
| 5,034,011 A | 7/1991 | Howland |
| 5,053,038 A | 10/1991 | Sheehan |
| 5,290,289 A | 3/1994 | Sanders et al. |
| 5,480,401 A | 1/1996 | Navas |
| 5,562,737 A | 10/1996 | Graf |
| 5,593,408 A | 1/1997 | Gayet et al. |
| 5,700,292 A | 12/1997 | Margulies |
| 5,728,098 A | 3/1998 | Sherman et al. |
| 5,797,911 A | 8/1998 | Sherman et al. |
| 5,853,414 A | 12/1998 | Groiso |
| 5,879,350 A | 3/1999 | Sherman et al. |
| 5,885,286 A | 3/1999 | Sherman et al. |
| 5,891,145 A | 4/1999 | Morrison et al. |
| 5,954,725 A | 9/1999 | Sherman et al. |
| 6,053,917 A | 4/2000 | Sherman et al. |
| 6,127,597 A | 10/2000 | Beyar et al. |
| 6,132,434 A | 10/2000 | Sherman et al. |
| 6,254,602 B1 | 7/2001 | Justis |
| 6,273,888 B1 | 8/2001 | Justis |
| 6,280,442 B1 | 8/2001 | Barker et al. |

(Continued)

FOREIGN PATENT DOCUMENTS

WO WO 95/02372 1/1995

(Continued)

OTHER PUBLICATIONS

Gruca, Adam, The Pathogenesis and Treatment of Idiopathic Scoliosis: A Preliminary Report, 1958; 40:570-584, The Journal of Bone and Joint Surgery, United States.

*Primary Examiner* — Eduardo C Robert
*Assistant Examiner* — Nicholas Plionis (57) ABSTRACT

The present application discloses methods for treating a spinal deformity. In one embodiment, an elongated member is attached to vertebral members with fasteners. A separate fastener may attach the elongated member to each of the vertebral members. The elongated member may apply a force to limit growth on one side of the vertebral members, such as a convex side of a scoliotic spine. Each fastener may be constructed to limit a direction of growth of the vertebral member thereby applying a specific, corrective force to the vertebral member. The fasteners may allow relative motion between adjacent vertebral members without losing the attachment between the vertebral members and the fasteners. The net result may be controlled modulation of growth to reduce and/or eliminate the spinal deformity through redirection of growth potential.

6 Claims, 7 Drawing Sheets

U.S. PATENT DOCUMENTS

| | | |
|---|---|---|
| 6,287,308 B1 | 9/2001 | Betz et al. |
| 6,287,311 B1 | 9/2001 | Sherman et al. |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,454,773 B1 | 9/2002 | Sherman et al. |
| 6,471,703 B1 | 10/2002 | Ashman |
| 6,485,491 B1 | 11/2002 | Farris et al. |
| 6,530,929 B1 | 3/2003 | Justis et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,660,004 B2 | 12/2003 | Barker et al. |
| 6,709,434 B1 | 3/2004 | Gournay et al. |
| 6,746,450 B1 | 6/2004 | Wall et al. |
| 6,755,830 B2 | 6/2004 | Minfelde et al. |
| 6,835,205 B2 | 12/2004 | Atkinson et al. |
| 6,837,904 B2 | 1/2005 | Ralph et al. |
| 6,966,911 B2 | 11/2005 | Groiso |
| 6,974,478 B2 | 12/2005 | Reiley et al. |
| 7,052,497 B2 | 5/2006 | Sherman et al. |
| 7,074,239 B1 | 7/2006 | Cornwall et al. |
| 2002/0151895 A1 | 10/2002 | Soboleski et al. |
| 2003/0004512 A1 | 1/2003 | Farris et al. |
| 2003/0023241 A1 | 1/2003 | Drewry et al. |
| 2003/0088251 A1 | 5/2003 | Braun et al. |
| 2003/0153912 A1 | 8/2003 | Graf |
| 2004/0034351 A1 | 2/2004 | Sherman et al. |
| 2004/0102774 A1 | 5/2004 | Trieu |
| 2004/0116929 A1 | 6/2004 | Barker et al. |
| 2005/0021035 A1 | 1/2005 | Groiso |
| 2005/0080420 A1 | 4/2005 | Farris et al. |
| 2005/0171539 A1 | 8/2005 | Braun et al. |
| 2005/0216004 A1 | 9/2005 | Schwab |
| 2005/0234451 A1 | 10/2005 | Markworth |
| 2005/0283157 A1 | 12/2005 | Coates et al. |
| 2006/0100709 A1 | 5/2006 | Reiley |
| 2006/0116677 A1 | 6/2006 | Burd et al. |
| 2006/0155279 A1 | 7/2006 | Ogilvie |
| 2006/0235392 A1 | 10/2006 | Hammer et al. |
| 2006/0241594 A1 * | 10/2006 | McCarthy et al. .............. 606/61 |
| 2007/0016201 A1 * | 1/2007 | Freudiger ....................... 606/61 |
| 2008/0269805 A1 * | 10/2008 | Dekutoski et al. ............. 606/279 |

FOREIGN PATENT DOCUMENTS

WO  WO 2005/074825 A1  8/2005

* cited by examiner

DEVICES AND METHODS FOR CORRECTING SPINAL DEFORMITIES

BACKGROUND

The present application is directed to methods for correcting spinal deformities and, more particularly, to methods that apply a corrective force to one or more of the vertebral members.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Schuermann's kyphosis is another example of a spinal deformity that affects the normal alignment of the vertebral members.

SUMMARY

The present application discloses methods for treating a spinal deformity. In one embodiment, an elongated member is attached to vertebral members with fasteners. A separate fastener may attach the elongated member to each of the vertebral members. The elongated member may apply a force to limit growth on one side of the vertebral members, such as a convex side of a scoliotic spine. Each fastener may be constructed to limit a direction of growth of the vertebral member thereby applying a specific, corrective force to the vertebral member. The fasteners may allow relative motion between adjacent vertebral members without losing the attachment between the vertebral members and the fasteners. The net result may be controlled modulation of growth to reduce and/or eliminate the spinal deformity through redirection of growth potential.

DETAILED DESCRIPTION

The present application is directed to the use of multiple fasteners in combination with an elongated member to modulate growth in patients with a spinal deformity. The elongated member and fasteners provide relative motion between adjacent vertebral members without losing the attachment between the vertebral members and the fasteners. The device may redirect the inherent growth of the patient to reduce and/or eliminate the spinal deformity.

Figure 1:
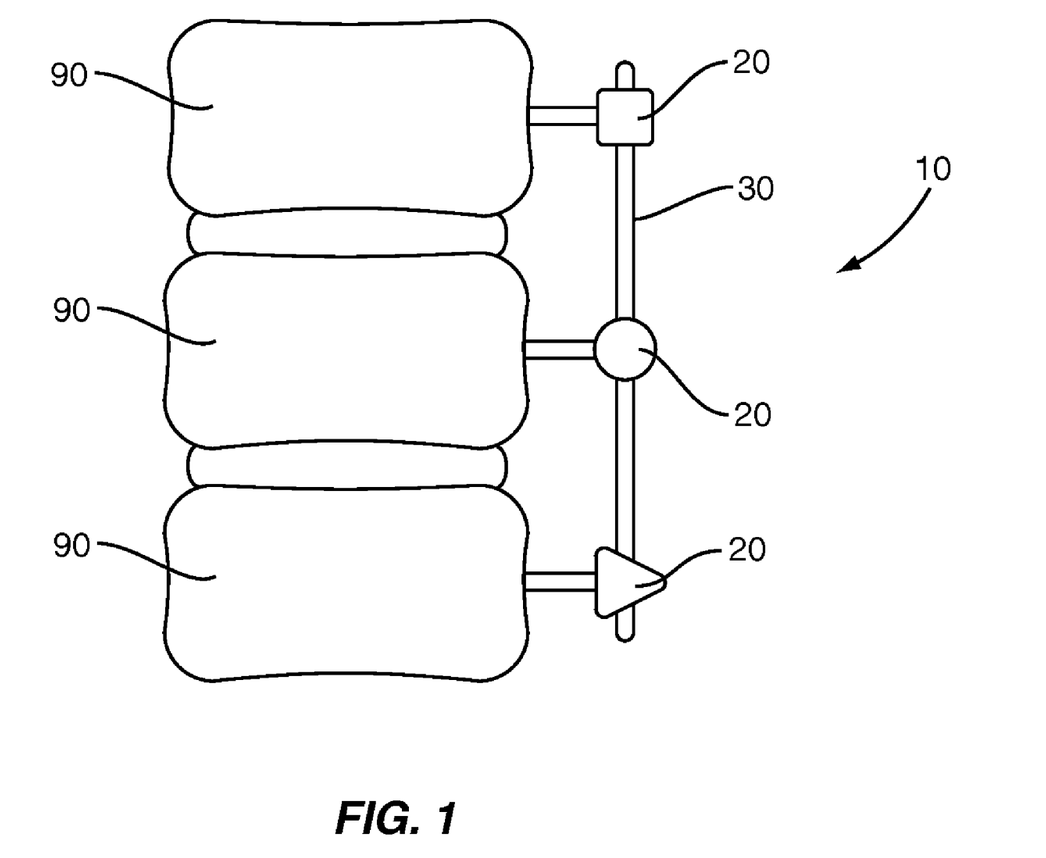
FIG. 1 is a schematic view of a device for treating the spine according to one embodiment.

FIG. 1 schematically illustrates one embodiment of a device 10 with fasteners 20 that attach the elongated member 30 to individual vertebral members 90. The fasteners 20 and member 30 create a tether to limit growth on one side of the vertebral members 90. Each fastener 20 is attached to a vertebral member 90 and limits motion of that vertebral member thereby applying corrective forces to treat the specific deformity of the vertebral member 90. As illustrated in FIG. 1, a first superior fastener 20 limits motion to a first range to correct the deformity of the attached first vertebral member 90. Likewise, the second intermediate fastener 20 limits motion to a second range to correct the deformity of the second vertebral member, and the third inferior fastener 20 a third range of motion to correct the corresponding third vertebral member 90. As the vertebral members 90 grow, the fasteners 20 and elongated member 30 guide the growth to reduce and/or eliminate the spinal deformity.

Figure 2:
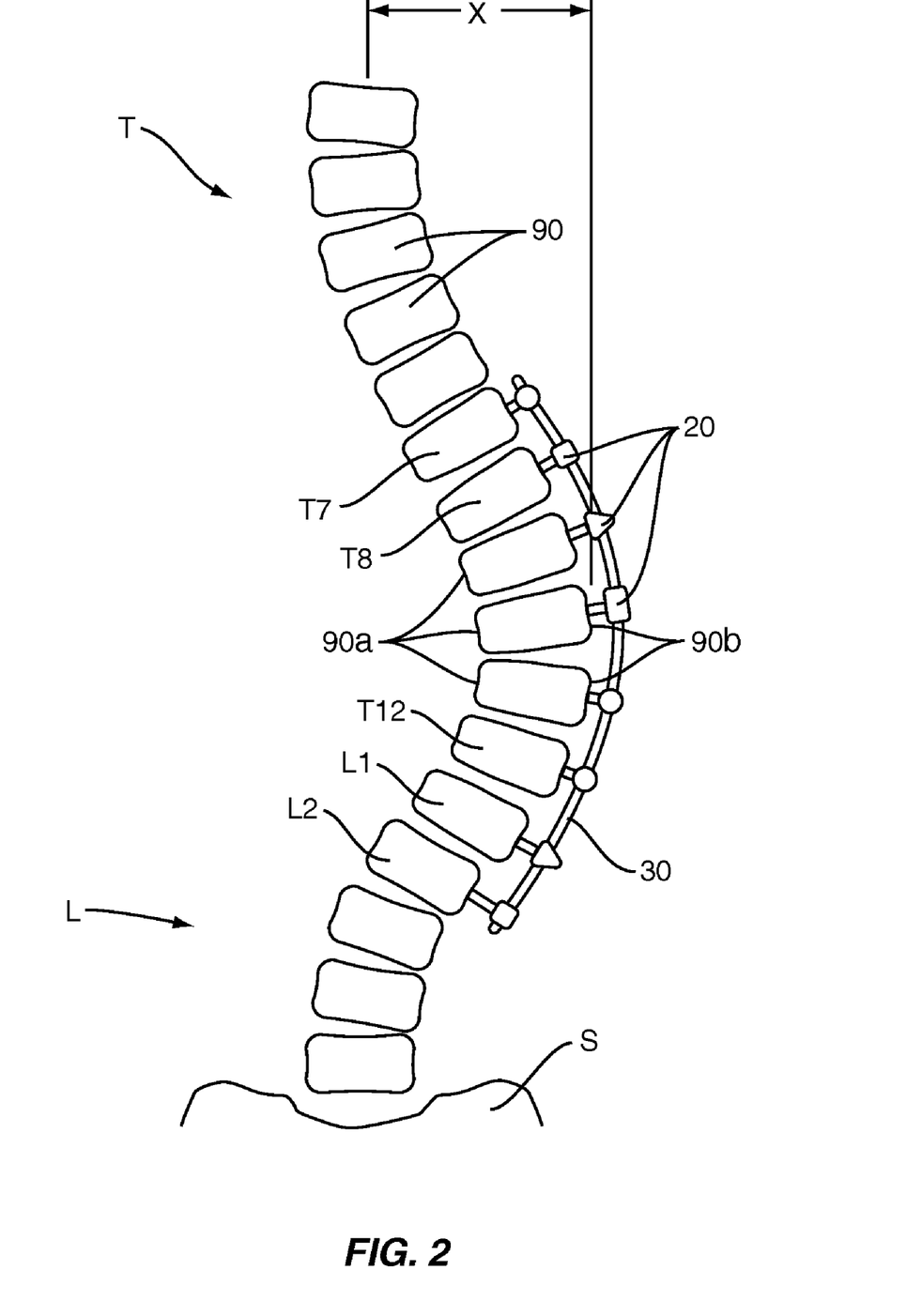
FIG. 2 is a schematic coronal view of a device attached to a scoliotic spine according to one embodiment.

FIG. 2 illustrates a patient's spine that includes a portion of the thoracic region T, the lumbar region L, and the sacrum S. This spine has a scoliotic curve with an apex of the curve being offset a distance X from its correct alignment in the coronal plane. The spine is deformed laterally so that the axes of the vertebral members 90 are displaced from the sagittal plane passing through a centerline of the patient. In the area of the lateral deformity, each of the vertebral members 90 includes a concave side 90a and a convex side 90b. An elongated member 30 is attached with fasteners 20 to the convex side 90b. The member 30 applies a compressive force to the convex side 90b of the vertebral members 90 to reduce and/or eliminate the spinal deformity. In addition, each of the fasteners 20 allows specific movement to the attached vertebral member 90. This combination of force and specific motion is used to reduced and/or eliminate the spinal deformity by redirecting the inherent growth potential of the spine.

Figure 3:
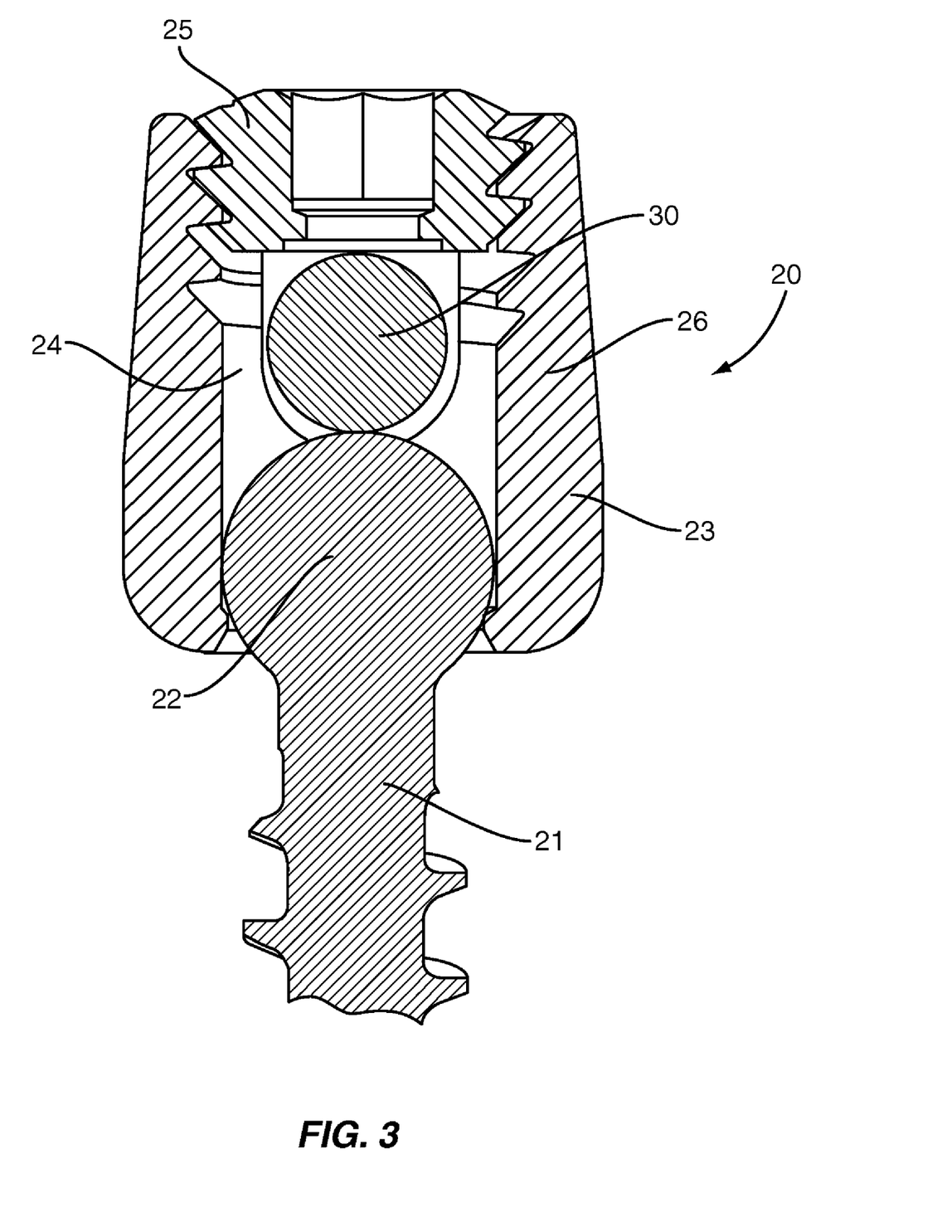
FIG. 3 is cross section view of a fastener according to one embodiment.

Various types of fasteners 20 may be used to connect the elongated member 30 to the vertebral members 90. FIG. 3 illustrates one embodiment of a multi-axial fastener 20. The fastener 20 includes a screw with a shaft 21 that mounts to the vertebral member 90 and a substantially spherical head 22. A saddle 23 is movably mounted to the head 22 and includes opposing arms 26 that form an interior space 24 sized to receive the member 30. A set screw 25 is threaded to the arms 26 to capture the member 30 within the interior space 24. The saddle 23 is pivotally and rotatably connected to the head 22. This connection provides multi-axial movement of the member 30 relative to the vertebral member 90 to which the shaft 21 is attached.

Figure 4A:
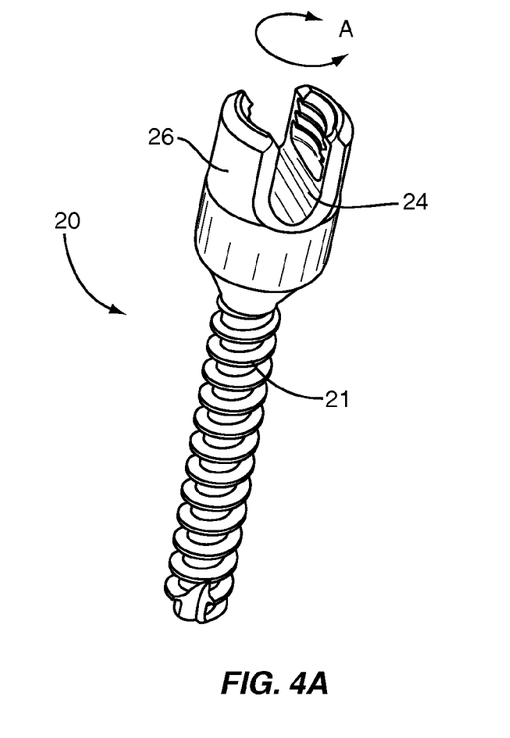
FIG. 4A is a perspective view of a fastener according to one embodiment.
Figure 4B:
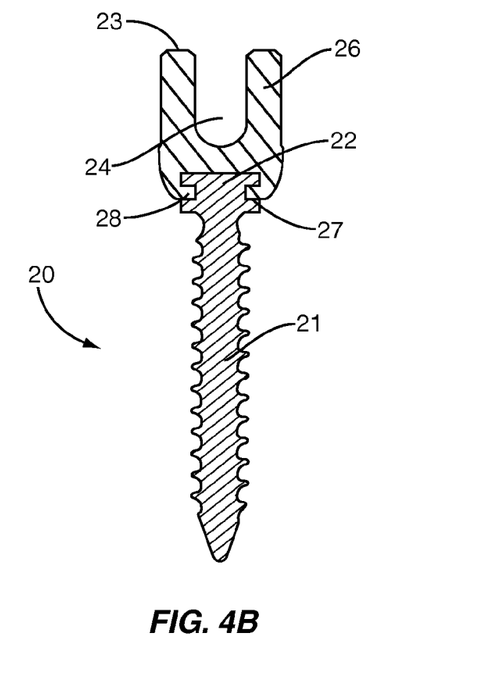
FIG. 4B is a cross section view of the fastener of FIG. 4A.

FIGS. 4A and 4B illustrate another embodiment of a fastener 20 that provides more limited motion. Screw includes a shaft 21 and a head 22 with a groove 27 that extends partially or completely around the head 22. Saddle 23 includes extensions 28 that fit within the groove 27. This construction provides the saddle to rotate on the head 22 and about the shaft 21 in the plane indicated by arrow A in FIG. 4A. The degree of motion of this embodiment is less than the fastener 20 illustrated in FIG. 3. A set screw (not illustrated in FIGS. 4A and 4B) threads to the arms 26 to capture the elongated member 30

Figure 4C:
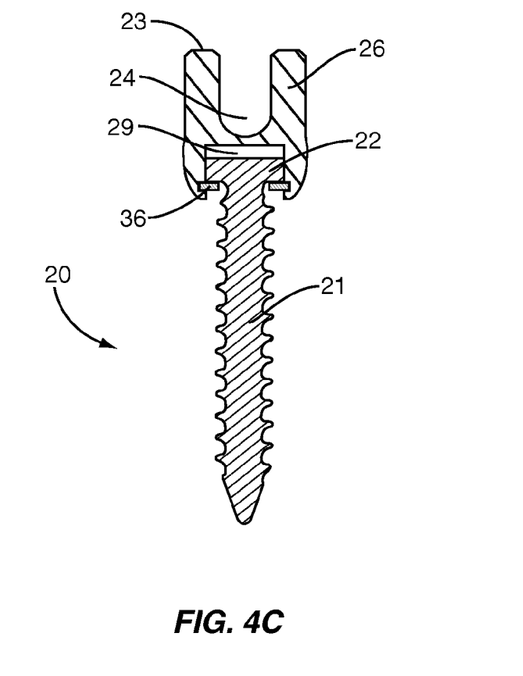
FIG. 4C is a cross section view of a fastener according to one embodiment.

FIG. 4C illustrates another embodiment of a fastener 20 with a screw that includes a shaft 21 and a head 22. Saddle 23 includes an opening 29 sized to receive the head 22. A ring 36 is mounted to the saddle 23 and extends across the opening 29 to maintain the position of the head 22.

Figure 5:
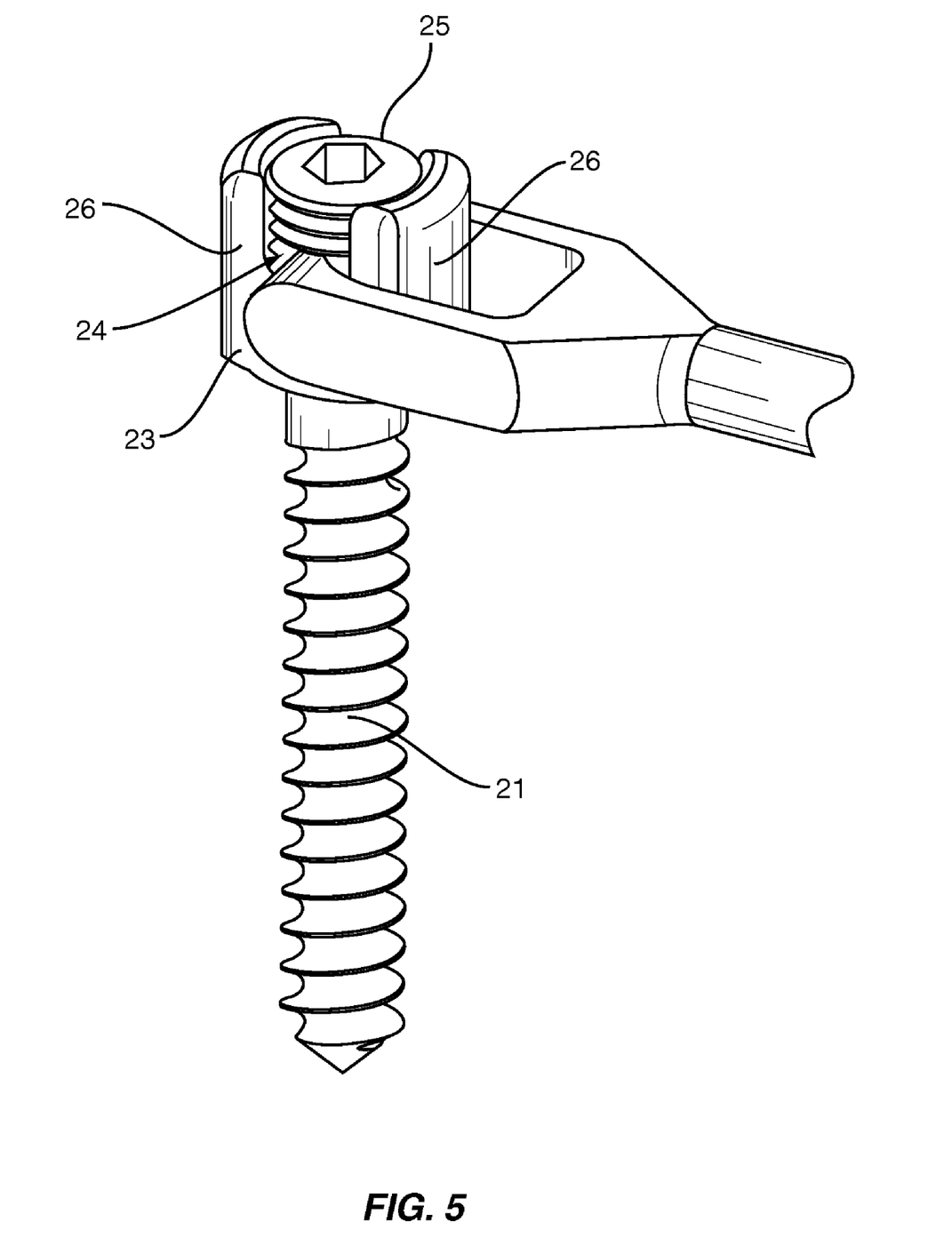
FIG. 5 is cross section view of a fastener according to one embodiment.

FIG. 5 illustrates another embodiment of a fastener 20. This embodiment includes the saddle 23 and shaft 21 constructed from a single member. Shaft 21 is mounted within a vertebral member 90 with the saddle 23 extending outwardly therefrom. Saddle 23 includes an opening 24 formed between arms 26 to hold the member 30. The fixed saddle 23 prevents movement of the member 30 relative to the attached vertebral member 90. In another similar embodiment, a pin extends through the arms 26 to pivotally position the member 30 within the opening 24. This structure provides for limited motion of the elongated member 30 relative to the fastener 20.

Figure 6:
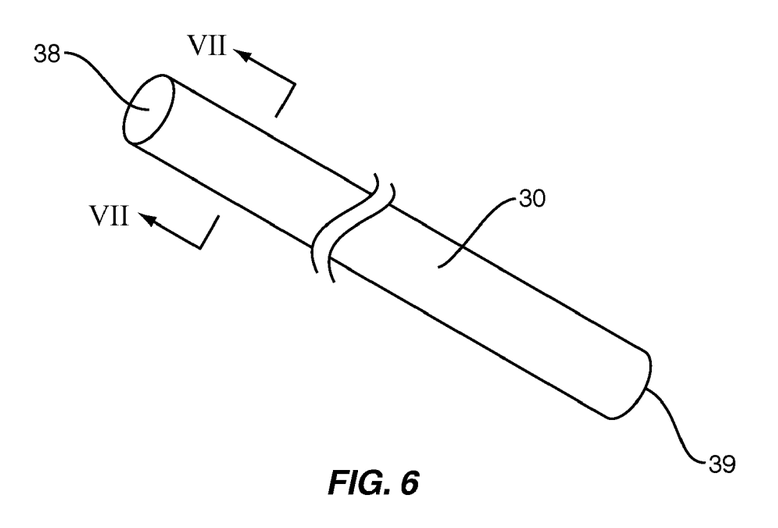
FIG. 6 is perspective view of an elongated member according to one embodiment.
Figure 7:
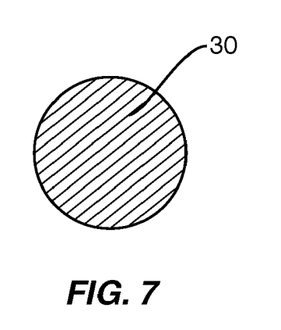
FIG. 7 is sectional view along line VII-VII of FIG. 6 illustrating a shape of the elongated member according to one embodiment.
Figure 8:
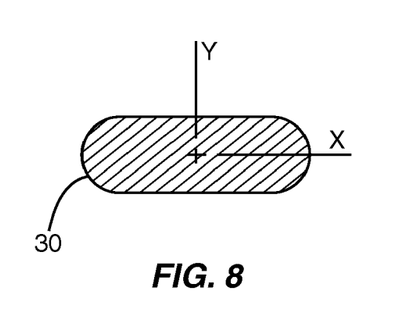
FIG. 8 is cross section view of an elongated member according to one embodiment.
Figure 9:
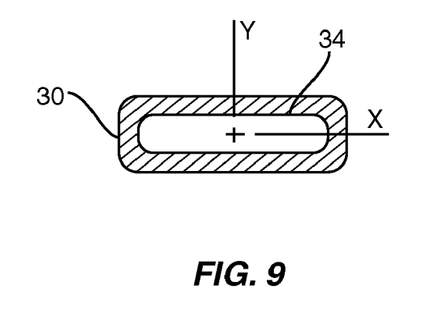
FIG. 9 is cross section view of an elongated member according to one embodiment.

FIG. 6 illustrates one embodiment of the elongated member 30 that includes a first end 38 and a second end 39. Member 30 may be substantially straight, include a continuous bend along the length between the ends 38, 39, include one or more discrete, curved sections. Member 30 may include a variety of cross sectional shapes. FIG. 7 illustrates one embodiment with a substantially circular cross section shape. FIG. 8 illustrates a substantially oval shape. FIG. 9 illustrates an embodiment with a substantially rectangular shape. The cross section shape may be substantially consistent along the length between the ends 38, 39, or different lengths may include different shapes.

Figure 10:
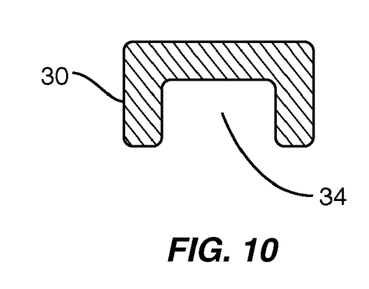
FIG. 10 is cross section view of an elongated member according to one embodiment.

In one embodiment, member 30 is substantially solid as illustrated in FIGS. 7 and 8. Member 30 may further include one or more openings 34. Openings 34 may be fully positioned within an interior of the member 30 as illustrated in FIG. 9, or may extend inward from an exterior side as illustrated in FIG. 10.

The elongated member 30 may be constructed from a variety of surgical grade materials. These include metals such as stainless steels, cobalt-chrome, titanium, and shape memory alloys. Non-metallic rods, including polymer rods made from materials such as polyetheretherketone (PEEK) and UHM-WPE, are also contemplated.

The structural characteristics of the member 30 provide vertebral bending in one or more directions, and prevent or limit bending in other directions. Using the example of FIG. 2, movement is provided within the sagittal plane and prevented or limited within the coronal plane. The structural characteristics may be dependent upon several factors, including the material choice of the member 30, and the cross section shape. The flexural rigidity, which is a measure of bending stiffness, is given by the equation:

$$\text{Flexural Rigidity} = E \times I \qquad (1)$$

where E is the modulus of elasticity or Young's Modulus for the rod material and I is the moment of inertia of a rod cross section about the bending axis. The modulus of elasticity varies by material and reflects the relationship between stress and strain for that material. As an illustrative example, titanium alloys generally possess a modulus of elasticity in the range between about 100-120 GPa. By way of comparison, implantable grade PEEK possesses a modulus of elasticity in the range between about 3-4 Gpa, which, incidentally, is close to that of cortical bone.

In general, an object's moment of inertia depends on its shape and the distribution of mass within that shape. The greater the concentration of material away from the object's centroid, the larger the moment of inertia. The centroid may be the center of mass for the shape assuming the material is uniform over the cross section. Using the embodiment of FIG. 8 as an example, since the width of the cross section area in the direction of the x axis is larger than the width in the direction of the y axis, it follows that the moment of inertia in the x-axis $I_x$ is larger than the moment of inertia in the y-axis $I_y$. This means that there is a greater resistance to bending in the x axis as compared to the y-axis. Using this member 30 within the embodiment of FIG. 2, the member 30 may be positioned with the x-axis substantially parallel to the coronal plane to prevent lateral bending and allow for flexion and extension. The surgeon may also elect to install the member 30 with the x and y axes oriented at angles other than aligned with the sagittal and coronal planes of the patient. Examples of members are disclosed in U.S. patent application Ser. No. 11/342,195 filed on Jan. 27, 2006 which is herein incorporated by reference.

Figure 11:
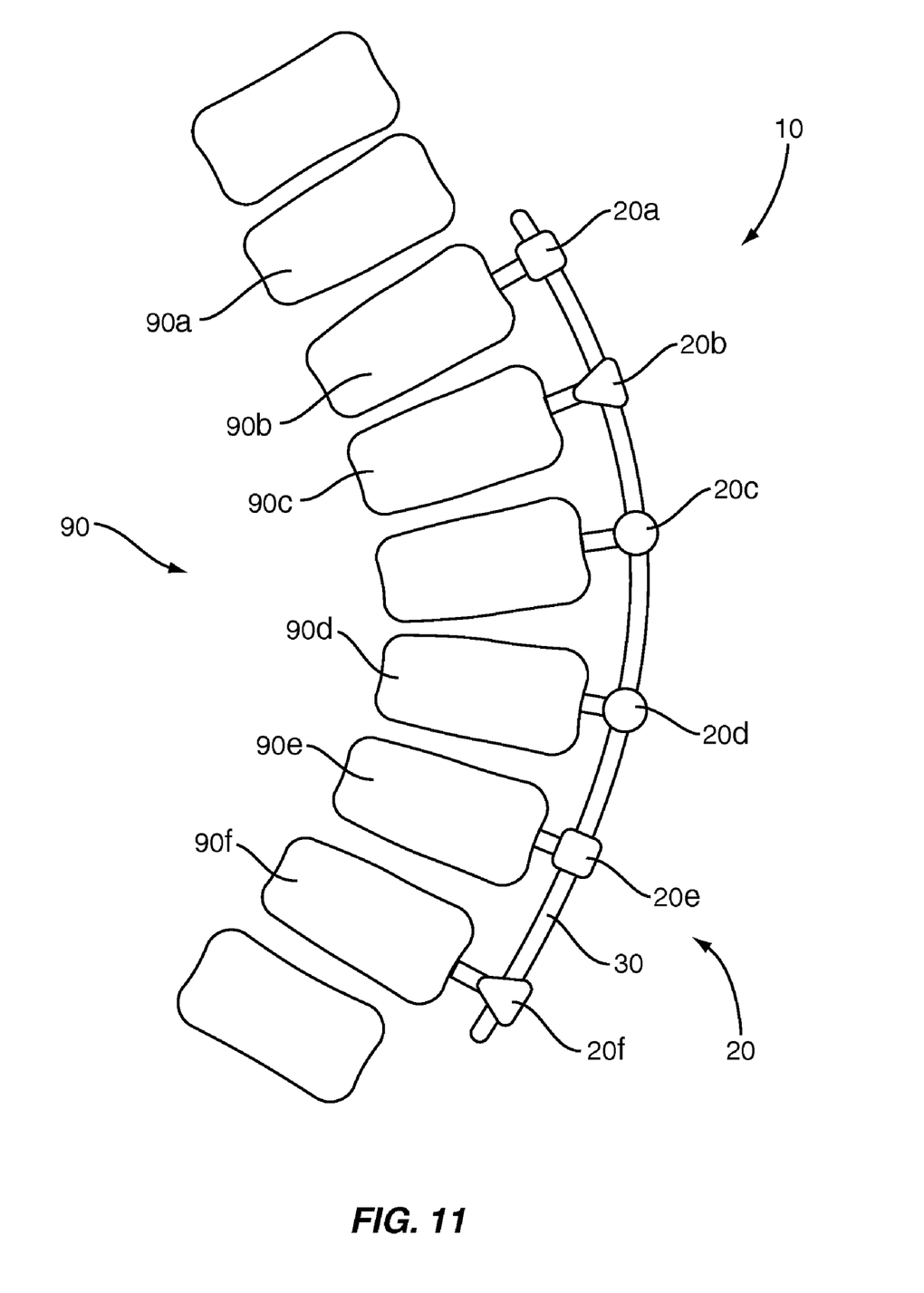
FIG. 11 is a schematic coronal view of a device attached to a scoliotic spine according to one embodiment.

FIG. 11 illustrates one embodiment of an elongated member 30 attached to vertebral members 90. Fasteners 20 are attached to each of the vertebral members 90. Specifically, first fastener 20a is attached to first vertebral member 90b, second fastener 20b to second vertebral member 90c, third fastener 20c to an adjacent third vertebral member, fourth fastener 20d to fourth vertebral member 90d, fifth fastener 20e to fifth vertebral member 90e, and sixth fastener 20f to sixth vertebral member 90f. In one embodiment, the elongated member 30 is attached to the convex side of the vertebral members 90. As the vertebral members 90 grow, elongated member 30 applies a compressive force that limits growth on the convex side while allowing growth on the concave side.

Each fastener 20 is constructed to limit the movement of the vertebral member 90 to which it is attached in some manner. This limiting provides for the fastener 20 to redirect and guide the force applied to the vertebral member 90 from the elongated member 30 during spinal growth to reduce and/or eliminate the deformity. In the embodiment of FIG. 11, first fastener 20a is designed to limit the movement of the first vertebral member 90a. As the vertebral member 90a grows, this motion limiting can cause a specific corrective force to be applied to the first vertebral member 90a. This corrective force can be specific for the first vertebral member 90a, and may be independent from the forces applied to the other vertebral members 90. Likewise, second fastener 20b limits motion of the second vertebral member 90b. This limiting can apply a specific corrective force to the second vertebral member 90b that may be independent of the other forces applied along the spine. The remaining fasteners 20c, 20d, 20d, 20e, 20f can be designed and positioned for the elongated member 30 to apply a specific corrective force to the vertebral member to which it is attached, respectively 90c, 90d, 90e, 90f.

The method may include a surgeon determining the specific corrective forces that are necessary to treat each of the individual vertebral members 90. This determination includes the type of fastener 20 that is attached to each vertebral member 90. Further, the orientation and positioning of each of the fasteners 20 on each vertebral member 90 should be determined. The determination may also include the type and orientation of the elongated member 30.

In one embodiment, a different fastener 20 is attached to each different vertebral member 90. In another embodiment, the same type of fastener 20 may be attached to two or more different vertebral members 90. Using FIG. 11 as an example, fasteners 20a and 20e are the same, fasteners 20b and 20f are the same, and fasteners 20c and 20d are the same.

In one embodiment, the elongated member 30 includes substantially constant stiffness properties along the length. In another embodiment, elongated member 30 includes two or more sections with different stiffness properties. The different properties may be caused by the material properties and shape of the member 30.

The above disclosure deals specifically with the broad range of device concepts envisioned for fusionless tethering of deformities in order to achieve permanent correction. The specifics with regard to the method are similarly broad. A wide range of spinal deformities could be managed. The primary indications will be progressive idiopathic scoliosis with or without sagittal deformity in either infantile or juvenile patients. The preferred patient population upon which to practice the present invention is prepubescent children (before growth spurt) less than ten years old. Other patient groups upon which the present invention may be practiced include adolescents from 10-12 years old with continued growth potential. It should be understood that fusionless tethering may be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. An anterior, minimally invasive (thoracoscopic) procedure can be carried out on the convex side of the spinal curve in order to prevent continued growth on that side of the curve. As the pre-growth spurt child approaches puberty, the untethered side of the spine will grow unconstrained, ultimately eliminating the curvature of the spine in the frontal plane. It is preferable to deliver this method of treatment in a minimally invasive approach using thoracoscopic instrumentation. It is contemplated as within the scope of the invention, however, that open use of these systems may be appropriate in some cases. It is further contemplated as within the scope of the invention that the procedure may be posterior as well as anterior, or some combination of both. Finally, it should be understood that if the procedure fails to correct the curve but does, in fact, prevent further progression (which includes increase in the magnitude of the curve) it can and should be considered successful.

It should be understood that the spinal deformity depicted in FIG. 2 is but one of many types of spinal deformities that can be addressed by the devices and techniques of the present application. Most commonly the devices and methods are expected to be used for either primary thoracic or thoracolumbar curves. They can be used for correction of the thoracic curve as an isolated curve, or the lumbar curve as an isolated curve. The devices may further be used in combination with the shortening of the opposite side of the vertebral member 90.

The devices and methods may be used to treat spinal deformities in the coronal plane, such as a scoliotic spine illustrated in FIG. 2. The devices and methods may also be used to treat deformities in the sagittal plane, such as a kyphotic spine or Scheurmann's kyphosis.

In one embodiment, the elongated member 30 is attached to a convex side of the vertebral members 90. However, elongated member 30 may be attached at different positions on the vertebral members 90. One embodiment includes accessing the spine from an anterior approach. Other applications contemplate other approaches, including posterior, postero-lateral, antero-lateral and lateral approaches to the spine, and accessing various regions of the spine, including the cervical, thoracic, lumbar and/or sacral regions.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The elongated member 20 may apply a force to arrest or minimize growth of the convex side 90b of the vertebral members 90, or alternatively, to simply prevent further deformity of the spine. The present embodiments are, therefore, to be considered in all respects as illustrative and not restrictive, and all changes coming within the meaning and equivalency range of the appended claims are intended to be embraced therein.

What is claimed is:

1. A method of treating a spinal deformity comprising:
   attaching a first fastener to a first vertebral member, the first fastener including a first anchor, a first receptacle, and a first connection that movably connects the first receptacle to the first anchor for the first receptacle to move relative to the first anchor within a first range of motion;
   attaching a second fastener to a second vertebral member, the second fastener including a second anchor, a second receptacle, and a second connection that movably connects the second receptacle to the second anchor for the second receptacle to move relative to the second anchor within a second range of motion, the second range of motion being smaller than the first range of motion, the second connection being different than the first connection;
   positioning an elongated member within the receptacles of the first and second fasteners, the elongated member including a first section with a first structural characteristic and stiffness that extends through the first receptacle and along the first vertebral member and a second section with a different structural characteristic and different stiffness that extends through the second receptacle and along the second vertebral member;
   during growth of the vertebral members, causing the first fastener to limit movement of the first vertebral member from growing and applying a first corrective force to the first vertebral member and causing the second fastener to limit movement of the second vertebral member from growing and applying a second corrective force to the second vertebral member, the second corrective force being different than the first corrective force.

2. The method of claim 1, further comprising positioning the elongated member along a first side of the vertebral members and limiting growth of the first side.

3. The method of claim 2, further comprising positioning the elongated member along a convex side of the vertebral members and limiting growth of the convex side.

4. The method of claim 1, wherein one of the first and second fasteners is a multi-axial fastener.

5. The method of claim 1, further comprising flexing the elongated member during growth of the vertebral members.

6. The method of claim 1, further comprising the first fastener allowing movement of the first vertebral member in more planes than the second fastener allows for the second vertebral member.

* * * * *